(12) United States Patent
Greveson (10) Patent No.: US 10,902,596 B2
(45) Date of Patent: Jan. 26, 2021

(54) TOMOGRAPHIC DATA ANALYSIS (71) Applicant: Brainomix Limited, Oxford (GB)

(72) Inventor: Eric Greveson, Oxford (GB)

(73) Assignee: BRAINOMIX LIMITED, Oxford (GB)

( * ) Notice: Subject to any disclaimer, the term of this patent is extended or adjusted under 35 U.S.C. 154(b) by 88 days.

(21) Appl. No.: 16/165,383

(22) Filed: Oct. 19, 2018

(65) Prior Publication Data

US 2019/0122363 A1  Apr. 25, 2019

(30) Foreign Application Priority Data

Oct. 23, 2017 (GB) .................................. 1717397.2

(51) Int. Cl.
*A61B 6/03* (2006.01)
*A61B 6/00* (2006.01)
(Continued)

(52) U.S. Cl.
CPC ............ *G06T 7/0014* (2013.01); *A61B 6/032* (2013.01); *A61B 6/501* (2013.01); *A61B 6/5205* (2013.01);
(Continued)

(58) Field of Classification Search
CPC .................................... A61B 5/00; A61B 5/02
See application file for complete search history.

(56) References Cited

U.S. PATENT DOCUMENTS 9,165,360 B1   10/2015   Bates et al.

2004/0122323 A1 * 6/2004 Vortman ................. A61N 7/02
600/459
(Continued)

FOREIGN PATENT DOCUMENTS

CN   103337065 B   3/2016
EP   2131212 A2   12/2009

OTHER PUBLICATIONS

United Kingdom Intellectual Property Office Search Report, United Kingdom Application No. 1717397.2 dated Aug. 23, 2018.
(Continued)

*Primary Examiner* — Joshua L Schwartz
(74) *Attorney, Agent, or Firm* — Snell & Wilmer L.L.P.

(57) ABSTRACT

Data from a tomographic scan (14) that provides three-dimensional information about a patient's brain comprises the steps of: filtering and re-sampling (21) the data to produce a three-dimensional image; performing registration (23) to align the three-dimensional image with a reference image (16), using 3-D rigid and/or non-rigid transformations; identifying (25) image features in the aligned image, to identify which voxels or regions of adjacent voxels correspond to image features that represent structures within the brain that are expected to be evident; classifying (26) each voxel within an identified image feature by a voxel score that corresponds to the difference between the attenuation of that voxel and the expected attenuation at that region of the brain; and deducing a cumulative score that combines the voxel scores from all the voxels of at least a region of the brain. This method can provide a medical professional with a rapid indication of the status of the brain tissue, which can be used to guide the selection of treatment to best improve the prospects for a patient, particularly a patient who has had an ischaemic stroke.

18 Claims, 3 Drawing Sheets

(51) Int. Cl.
   *G06T 11/60* (2006.01)
   *G06T 7/00* (2017.01)
   *G06T 7/37* (2017.01)

(52) U.S. Cl.
   CPC .............. *A61B 6/5217* (2013.01); *G06T 7/37* (2017.01); *G06T 11/60* (2013.01); *G06T 2200/04* (2013.01); *G06T 2200/24* (2013.01); *G06T 2207/10072* (2013.01); *G06T 2207/10081* (2013.01); *G06T 2207/20076* (2013.01); *G06T 2207/20081* (2013.01); *G06T 2207/30016* (2013.01)

(56) References Cited

U.S. PATENT DOCUMENTS

| | | | | |
|---|---|---|---|---|
| 2011/0160543 | A1* | 6/2011 | Parsey | A61B 5/4088 600/300 |
| 2013/0129168 | A1* | 5/2013 | Ross | A61B 5/4842 382/128 |
| 2015/0080703 | A1* | 3/2015 | Reiman | G06F 19/00 600/409 |
| 2016/0335768 | A1 | 11/2016 | Mori et al. | |

OTHER PUBLICATIONS

Chan et al., "Computer Aided Detection of Small Acute Intracranial Hemorrhage on Computer Tomography of Brain", Computerized Medical Imaging and Graphics, Pergamon Press, New York, NY, US, vol. 31, No. 4-5, Apr. 20, 2007, pp. 285-298.
International Search Report and Written Opinion, for Application No. PCT/GB2018/053054, dated Dec. 5, 2018.

\* cited by examiner

TOMOGRAPHIC DATA ANALYSIS

This patent application claims priority to GB 1717397.2, filed 2017 Oct. 23.

The present invention relates to a method for analysing data corresponding to a tomographic image, for example a tomographic image of a patient's head, to assist a medical professional diagnosing the medical condition and of the patient, and identifying suitable treatment.

The invention is particularly suitable for a diagnosis of a patient who has recently had a stroke. There are two different types of stroke: a haemorrhagic stroke, in which there is bleeding within the brain; and an ischaemic stroke in which there is a blockage of a blood vessel which reduces or prevents blood flow to a region of the brain. A haemorrhagic stroke is detectable in a computed tomographic image of the brain because the blood is denser than the brain tissue, and therefore attenuates x-rays to a greater extent; while an ischaemic stroke is detectable in a computed tomographic image of the brain because the cause of the blockage is a blood clot which may be detectable because of its greater x-ray attenuation, and because the region of the brain in which cells have died as a consequence of the lack of oxygen decreases in density towards that of water, and therefore becomes detectable through reduced x-ray attenuation. The present invention is particularly suitable for diagnosing ischaemic strokes in early stages after the onset of the stroke, when treatment to remove the blockage can have a significant effect in the subsequent recovery of the patient, in preventing further brain damage.

The invention utilises data obtained by computed tomography. Tomography is a technique for obtaining a cross-sectional image of an object, in particular by measuring x-ray attenuation along multiple paths through the cross-section by scanning a source and an opposed sensor around the object and deducing the cross-sectional image by computation. Along any one path, the observed attenuation is determined by the cumulative attenuation of each successive portion of the object that makes up the path. Although computed tomography was originally envisaged for obtaining two-dimensional images, information about the three-dimensional structure of an object can be obtained by combining information from multiple two-dimensional images in closely spaced planes, or by a performing a scan along a helical path around the object. To obtain a two-dimensional image, the cross-sectional area is broken down into pixels, and the computation calculates attenuation for each pixel. The smaller the pixels the greater the potential resolution of the image, but the more calculation is required, and the more noise will be present in the image; by way of example each pixel may be 1.0 mm square, or 0.5 mm square. To obtain a three-dimensional image, data from multiple two-dimensional images are combined, and the values of attenuation are deduced for "volumetric pixels" usually referred to as "voxels". The height of each voxel (i.e. the dimension orthogonal to the plane of the two-dimensional image) may differ from the spacing between the planes of successive two-dimensional images, for example it may be larger than the spacing so that the calculated attenuation of each voxel incorporates data from a plurality of two-dimensional images. For example each voxel might be between 2 mm and 8 mm high, for example 5 mm high.

When a patient who has had an ischaemic stroke arrives in hospital, it is important for decisions on the appropriate treatment to be made both accurately and rapidly, as faster treatment can minimise the amount of brain tissue that is ultimately affected by the stroke. The medical professional ideally needs to know where the blockage of the blood vessel is, where any dead brain tissue is, and which regions of brain tissue can potentially be saved. Although one blood vessel may have been blocked, so depriving one region of brain tissue of oxygen, there may be surrounding regions of the brain that continue to obtain oxygen by perfusion from collateral arteries. It may be possible therefore to treat the patient so as to ensure that these surrounding regions do not deteriorate further, if treatment is provided soon enough. Computed tomography is a comparatively rapid process, as a scan of a patient's skull can be performed in just a few minutes, and rapidly analysed in accordance with the present invention.

Currently the images obtained by computed tomography (CT) scanning may be assessed by the medical professional by using the ASPECTS scoring system ("Alberta Stroke Programme Early CT Score"). This involves the medical professional's subjective evaluation of early ischaemic damage in ten regions of the brain, on the basis of CT images, in particular considering the basal ganglia level, where the caudate nucleus and putamen should be visible, and then the supraganglionic level, which includes the corona radiata and centrum semiovale. Some of the regions, such as the caudate, the insula, the internal capsule, and the lentiform nucleus are brain structures that will be recognisable in the image, whereas other regions are merely convenient subdivisions of the cortex, named M1-M6 in the ASPECTS method. The ASPECTS method provides an approximate quantification of the extent of ischaemia, but does not take into account the severity of ischaemia within a particular region, or the functional relevance of each brain area. An improved method for analysing such images would be desirable.

According to the present invention, in a first aspect, there is provided a method of analysing data from a tomographic scan that provides three-dimensional information about a patient's brain, the method comprising the steps of:

processing the data to produce a three-dimensional image;

performing registration to align the three-dimensional image with a reference image, using 3-D rigid and/or non-rigid transformations;

identifying regions in the aligned image that correspond to structures within the brain that are expected to be evident;

classifying each voxel within an identified region by a voxel score that corresponds to the difference between the attenuation of that voxel and the expected attenuation at that region of the brain; and deducing a cumulative score that combines the voxel scores from all the voxels of at least a region of the brain.

Unlike the ASPECTS score, the present invention analyses the images voxel-by-voxel, and does not require the use of any arbitrary subdivisions of the brain tissue.

The step of processing the data may involve filtering and may also involve re-sampling, depending on the nature of the data from the apparatus performing the tomographic scan.

The attenuation associated with a voxel is typically measured in Hounsfield units (HU), which gives a linear scale in which the radiodensity of distilled water is 0 HU, while the radiodensity of air is −1000 HU. By way of example the radiodensity of bone will be more than 200 HU, that of a blood clot may be about 60 HU, while that of healthy grey matter brain tissue is about 40 HU. Preferably the voxel score is calculated in a way that indicates the likelihood or probability of damage to that region of the brain, and this may for example be a probability value between 0 and 1. For example in the context of an ischaemic stroke, a decrease of attenuation by say 3 HU in a particular region may be indicative of significant stroke damage, while in a different region a decrease of attenuation of say 6 HU may be indicative of significant stroke damage, and in each case this may be given a voxel score of 1 to indicate certainty. Regions of the brain in which the change in attenuation is even greater than that indicative of significant stroke damage would not be given a greater voxel score; and those voxels where there is uncertainty as to whether or not the change is significant would have a voxel score less than 1.

The voxel score may also be adjusted or weighted to take account of the functional relevance of that part of the brain, by associating each voxel with a weight indicating the importance of the corresponding portion of brain tissue to patient outcome and disability. The cumulative score would then combine the weighted voxel scores.

The cumulative score would therefore be clinically useful in indicating the extent to which irreversible damage to the brain has already occurred, and hence whether treatment to remove the clot causing the ischaemic stroke would have any benefit to the patient.

In addition the medical professional may be provided with two-dimensional images calculated from the three-dimensional information, for example corresponding to the aligned images, on which the voxel scores are superimposed. For example the two-dimensional images may be in black and white, as is conventional for tomographic images, and the voxel scores may be superimposed on the image in a colour, such as red, the intensity of the colour representing the voxel score. This draws attention to those regions of the brain that appear to have suffered damage.

In the context of an ischaemic stroke, the clot itself would produce an increase in attenuation whereas the resultant cell damage produces a decrease in attenuation. In this case the voxel scores for voxels in which there is an increase of attenuation may be superimposed on the two-dimensional image in a different colour to that used to mark where there is a decrease in attenuation. For example where the voxel scores for ischaemic damage are shown red, the clot may be highlighted in blue.

It will be appreciated that from computed-tomography scans of multiple people who are not suffering from any brain injury, a reference image can be derived showing the appearance, on average, of such a scan, and typically the reference image will be aligned with the centre plane of the skull extending across the image from the middle of the top of the image to the middle of the bottom. Multiple reference images can be generated, each corresponding to a group of people whose brains have similar structures, for example by averaging images from a group of people of a similar age and with a similar size of skull. Similarly, in such a reference image, brain structures can be identified, and the normal or average values of attenuation of voxels within these brain structures can be determined and be taken as the expected attenuation within a voxel of a patient who has had a stroke. Alternatively, the expected attenuation within a region of the brain may be deduced from measurement of attenuation at other parts of the same image. For example, an ischaemic stroke usually causes damage only to one half of the brain, so a comparison may be made between corresponding regions on opposite sides of the brain.

In a second aspect, the invention provides a method for obtaining an assessment of the severity and location of a stroke in a patient, the method comprising:

performing a three-dimensional computed-tomography scan of the patient's head;

processing data from the computed-tomography scan to produce a three-dimensional image;

performing registration to align the three-dimensional image with a reference image, using 3-D rigid and/or non-rigid transformations;

identifying regions in the aligned image that correspond to structures within the brain that are expected to be evident;

classifying each voxel or group of voxels within an identified region by a voxel score that is derived from the difference between the attenuation of that voxel and the expected attenuation at that region of the brain; and deducing a cumulative score that combines the voxel scores from all the voxels of at least a region of the brain.

In a third aspect the invention provides a method for displaying information about the severity and location of a stroke in a patient, comprising:

performing a three-dimensional computed-tomography scan of the patient's head;

processing data from the computed-tomography scan to produce a three-dimensional image;

performing registration to align the three-dimensional image with a reference image, using 3-D rigid and/or non-rigid transformations, to produce aligned images in multiple planes through the patient's skull;

identifying regions in the aligned image that correspond to structures within the brain that are expected to be evident;

classifying each voxel within an identified region by a voxel score that is derived from the difference between the attenuation of that voxel and the expected attenuation at that region of the brain; and displaying two-dimensional images calculated from the three-dimensional image data, on which the voxel scores are superimposed.

As previously mentioned, the voxel scores may be superimposed on the image in a colour, such as red, the intensity of the colour representing the voxel score. This draws attention to those regions of the brain that appear to have suffered damage.

The invention will now be further and more particularly described, by way of example only, and with reference to the accompanying drawings, in which.

Figure 1:
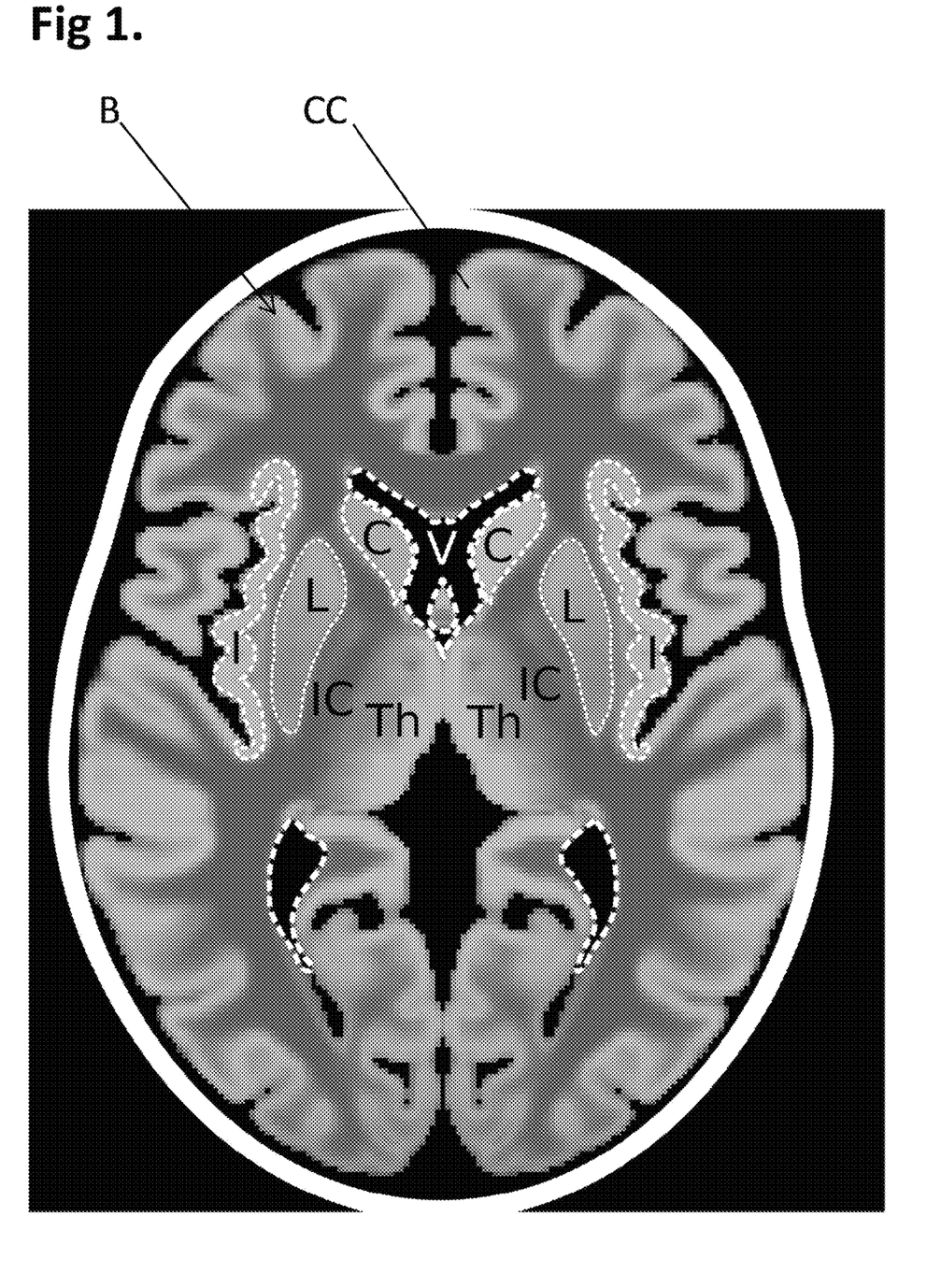
FIG. 1 shows a schematic cross-section of a human brain in which some of the brain features are indicated.

Referring now to FIG. 1, this shows a schematic cross-section of a human brain B at the level of the basal ganglia. The outer part of the human brain B is the cerebral cortex CC, and in this view the caudate nucleus C, the insular ribbon I, the internal capsule IC, the thalamus Th, the ventricle V, and the lentiform nucleus L can also be seen. These brain features will be observed in a number of successive scans during computed tomography, because of their vertical extent. Furthermore, with each of these brain features the radiodensity or x-ray attenuation is comparatively uniform.

Figure 2:
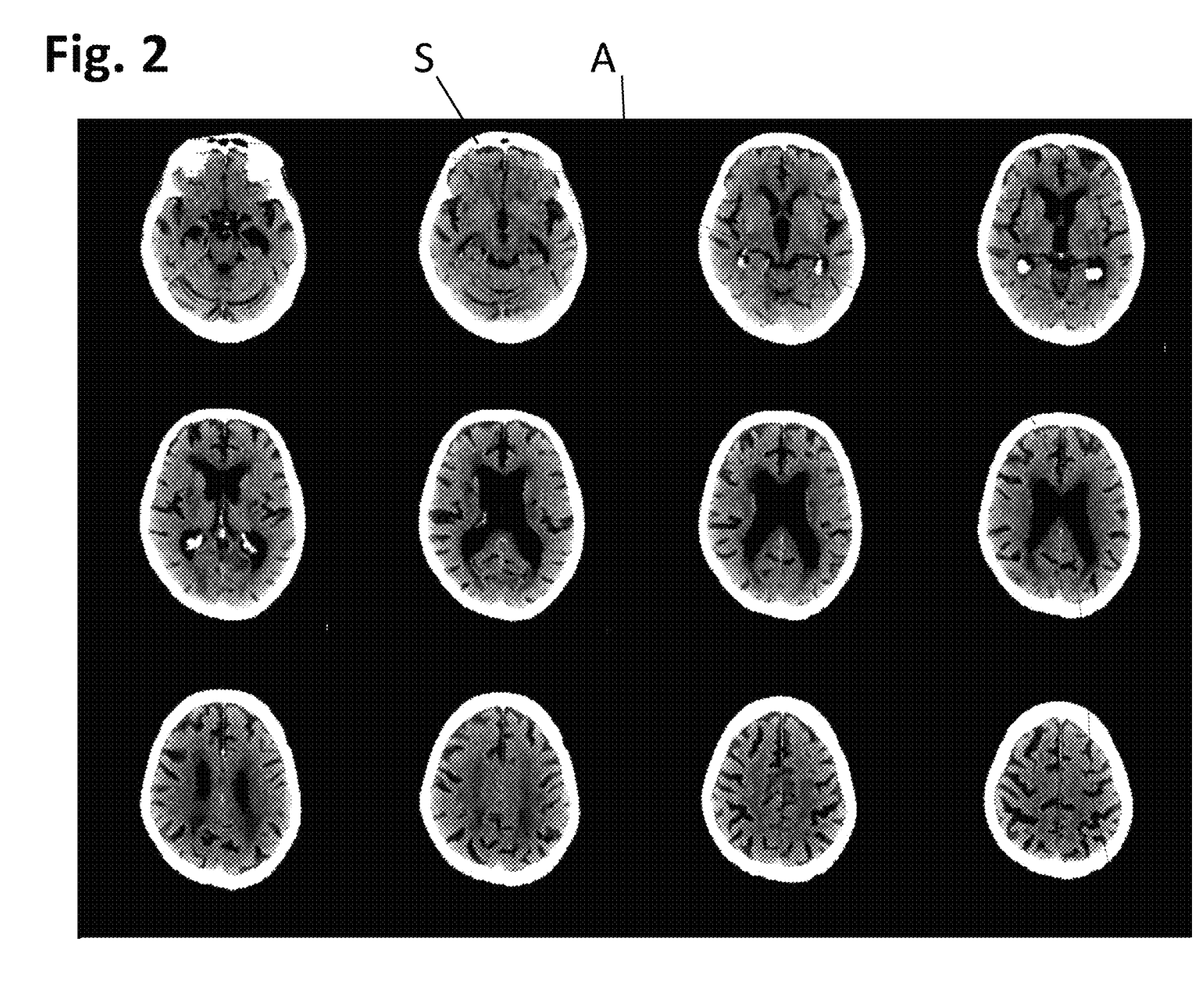
FIG. 2 shows CT scanned images at successive parallel planes within a patient's skull.

Referring now to FIG. 2, this shows a sequence of computed tomography scans in successive planes, which in this example are at 6 mm vertical spacing, of the skull and brain of a patient who has suffered a stroke. The white region surrounding the brain is the skull S, which is of high radiodensity, while the surrounding dark zone is air A, which is of very low radiodensity; this use of a greyscale corresponds to that obtained with a conventional x-ray, and is the normal way of representing computed tomography images.

However, since for studying the brain any regions that have a radiodensity greater than about 80 HU are irrelevant, as are any regions that have a radiodensity less than 0 HU, the images are shown with the greyscale corresponding to a restricted range of values of radiodensity. For example the image may be displayed in such a way that 256 grey levels correspond to the range between 0 and 80 HU, so that any value below 0 HU is black, and any value above 80 HU is white. The greyscale may correspond to a somewhat different range of values of radiodensity (for example between 17 HU and 53 HU instead of 0 HU to 80 HU), but in any event matching the grey scale to the range of values of radiodensity that is of interest in a particular context may enable the medical professional to see features of the brain within the computed tomography image more easily. This is a standard aspect of the current technology for viewing computed tomography images.

The image shown in FIG. 1 gives a schematic representation of what might be expected in a cross-section of a typical or average brain, but it will be appreciated that an individual patient will not have a brain with exactly the appearance shown in FIG. 1. For example some aspects of brain structure, such as the size of the ventricle V, are dependent on various factors such as the patient's age. As regards the images in FIG. 2, the one that corresponds most closely to FIG. 1 is the first view in the second row of images of FIG. 2. It will also be appreciated that all the images of FIG. 2 have been aligned so that the centre plane of the brain is vertical.

Figure 3:
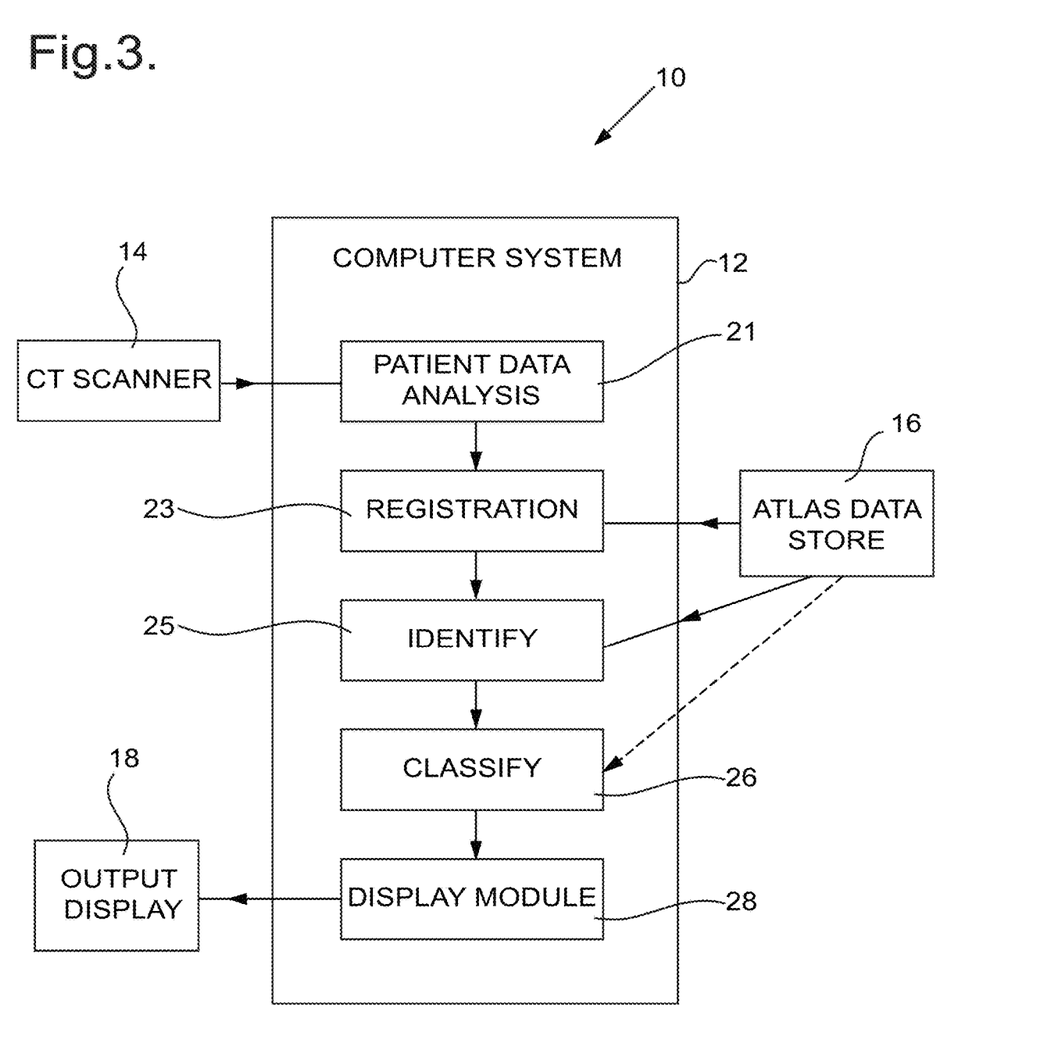
FIG. 3 shows a schematic diagram of apparatus for performing the method.

Referring now to FIG. 3, this shows a schematic image of apparatus 10 for performing the method of the invention. The apparatus 10 includes a computer system 12, a computer tomography scanner 14, an atlas data store 16 and a display 18. The computer system 12 includes a patient data analysis module 21, a registration module 23, an identification module 25, a classification module 26 and a display control module 28. The computed tomography scanner 14 operates in a known way to perform a scan of the patient's head which may be a helical scan or multiple axially-spaced scans, and from the data on the attenuation obtained during the scan reconstructs a three-dimensional image at a preset slice thickness (typically between 0.6 mm and 4 mm). The data from the scanner 14 representing the reconstructed three-dimensional image is then sent via a DICOM file or other network protocol to the computer system 12 for analysis. The data from the scanner 14 relating to the scan of a patient's head is supplied to the patient data analysis module 21 in which the data is processed to provide a three-dimensional image, with attenuation data for each voxel within the image of the patient's brain and skull. Depending on the nature of the data provided by the scanner 14, it may be necessary to perform filtering of the data, and re-sampling, in order to be able to obtain a satisfactory three-dimensional image.

The data representing the three-dimensional image is then supplied to the registration engine 23, which aligns the image with a standard alignment, typically that in which the centre plane of the brain is vertical (as in each of the images of FIG. 1 and FIG. 2). This alignment may utilise 3-D rigid and/or non-rigid transformations, and essentially involves rotating the image to bring it into the required alignment. This alignment may utilise a comparison to a standard brain image stored in the atlas data store 16.

The atlas data store 16 may store a single standardised three-dimensional image of a human brain averaged over many people, or more preferably stores multiple standardised three-dimensional images of brains, each averaged over different groups of people or taken from different individuals. As mentioned above, brain structure is at least partly dependent on age; so preferably the atlas data store 16 stores multiple different standardised three-dimensional images, each representing the average for a group of people that have similar brain structure, for example a group of people of similar ages. Each such standardised three-dimensional image is pre-coded to identify the different structures within the brain image, and this identification coding may be performed by a skilled radiologist. In addition, the atlas data store 16 may include, for each different structure within the brain image, information on the extent to which damage to that brain structure has an impact on subsequent recovery of the patient, that is to say the functional relevance of that part of the brain to patient outcome and subsequent disability. This information could be obtained from published clinical studies regarding functional relevance of stroke lesions.

The data representing the aligned three-dimensional image is then supplied to the identification module 25, in which image features are identified according to what brain structure they represent, by comparison with the most similar standardised three-dimensional image from the atlas data store 16. This may also require use of 3-D rigid and/or non-rigid transformations to bring into conformity the aligned three-dimensional image and the standardised three-dimensional image from the atlas data store 16. For example this may involve a deformable registration based on a normalised cross-correlation metric.

The data representing the aligned three-dimensional image along with the data about the image features is then provided to the classification module 26, in which each voxel within the aligned three-dimensional image is classified and given a voxel score that is indicative of the difference between the attenuation of that voxel and the expected attenuation at that region of the brain, and so may indicate early signs of ischaemia. This classification may be carried out in a number of different ways. The classification may compare the attenuation of an individual voxel to the corresponding voxel in the most similar standardised or averaged three-dimensional image from the atlas data store 16, as indicated by a broken line in FIG. 3. Alternatively the classification module 26 may perform the classification on the basis of a comparison between corresponding voxels on the left and right hand sides of the aligned image so as to compare individual voxels on opposite sides of the brain that form part of the same type of brain structure and can therefore be expected to have substantially equal values of attenuation. Alternatively the classification may compare a voxel from a particular structure with the average for the voxels that form the same type of structure on the opposite side of the brain. For example, where a particular voxel is identified as forming part of the caudate nucleus C, a comparison may be made with an average for all the voxels that have been identified as forming part of the caudate nucleus C on the other side of the brain; where a particular voxel is identified as forming part of the grey matter of the brain, a comparison may be made with an average for all the voxels that have been identified as forming part of the grey matter on the opposite side of the brain; and similarly where a particular voxel is identified as forming part of the white matter of the brain, a comparison may be made with an average for all the voxels that have been identified as forming part of the white matter on the opposite side of the brain.

It will be appreciated that the values of attenuation for particular regions of brain material such as grey matter or white matter can be calculated in a range of different ways, for example k-means clustering, GMMs (Gaussian mixture models), thresholding to mask voxels, or a combination of approaches like these, instead of simple averaging.

In every case the voxel score for each voxel takes into account the significance of the observed difference, that is to say how likely it is that the observed difference indicates damage to the corresponding region of the brain due to a stroke, in particular an ischaemic stroke. The voxel score may for example be a probability value between 0 and 1. Such a probability value does not necessarily correspond directly to the observed difference of attenuation, because a decrease of attenuation by say 3 HU in a particular region or brain structure may be indicative of significant stroke damage, whereas in a different region or brain structure significant stroke damage may be indicated by a decrease of attenuation of say 6 HU; in each case the voxel may be given a voxel score of 1 to indicate certainty. Regions of the brain in which the change in attenuation is even greater than that indicative of significant stroke damage would not be given a greater voxel score, so that the maximum value is 1. The only voxels that would be given a voxel score between 0 and 1 would be those voxels where there is uncertainty as to whether or not the change is significant.

The voxel score for an individual voxel or a group of adjacent voxels may be derived by the classification module 26 directly from the observed difference in attenuation, or may be derived indirectly, for example being computed by training a machine learning classifier on an annotated training dataset. The classification module 26 may interpret image features and take into account local image statistics. A variety of different types of classifiers are known and would be suitable for use as the classification module 26, for example a random forest classifier, or a neural network, or an SVM (support vector machine) classifier. The role of the classification module 26 is to use observed differences in attenuation to provide an indication of the likelihood of ischaemic damage.

The resultant information can be then supplied to the display module 28, and so presented on the output display 18. The information may be displayed in different ways. In one case the aligned image data is displayed on the output display 18 as a conventional two-dimensional black and white image like the images shown in FIGS. 1 and 2, but for each voxel within the displayed image the corresponding voxel score may be displayed in colour. For example the voxel score may be displayed in red, the intensity of the colour of each pixel in the displayed image depending on the corresponding voxel score. In this way the likelihood of damage at each different voxel within the displayed two-dimensional brain image is superimposed on the corresponding pixel in the two-dimensional black-and-white image. In this way the radiologist or other medical professional can view any desired sectional view through the patient's brain, and in each such view the medical professional is presented with a clear indication of which portions of the patient's brain are severely damaged, and which portions are only slightly damaged and where recovery of brain function may be feasible if appropriate steps are taken.

As another way of displaying the information, the voxel scores for each voxel within the entire three-dimensional image may be added together to provide a cumulative score. This cumulative score may be scaled to take into account the number of voxels within the three-dimensional image of the brain, for example by dividing the cumulative score by the number of voxels. Thus the voxel scores may be processed to provide a numerical value which is indicative of the degree of damage, either in total or on average, throughout the brain.

In a further modification the voxel score may be calculated in such a way as to take into account the relative significance to the patient's subsequent recovery of the region of the brain in which the damage has occurred. That is to say each voxel score may be weighted to take account of the functional relevance of that part of the brain, by multiplying the probability of damage for each voxel (as assessed above) with a weight that indicates the importance of the corresponding portion of brain tissue to patient outcome and subsequent disability. The cumulative score would then combine the weighted voxel scores.

It will thus be appreciated that the method of the invention provides the medical professional with a rapid and accurate way of determining the extent of damage to the patient's brain, and in the case of an ischaemic stroke to determine if treatment to remove the blood clot that has caused the blockage has any likelihood of altering the outcome for the patient. This enables the medical professional to decide what treatment is appropriate.

It will also be appreciated that the individual steps of the overall method may be carried out in a range of different ways. For example, where data filtering is required this may use Gaussian blur, bilateral filtering, or total variation methods. The alignment step may include rigid or non-rigid transformations, but in each case a number of variants are possible, for example in the case of rigid transformations the optimiser may be a gradient descent, or a Newtonian; when it comes to metric choices this may utilise cross correlation, mean squared error, or mutual information etc. As regards identification of brain regions, this can use simple atlas label lookups, or include morphology masking, classifiers or voting methods. Furthermore the display may use colour, greyscale intensities, a simulated 3-D display, and may display either weighted scores or unweighted scores.

The invention claimed is:

1. A computer-implemented method for deriving a score representative of extent and progression of ischemia in a patient's brain, by analysing data from a tomographic scan that provides three-dimensional information about the patient's brain, the method comprising the steps of:

processing the data to produce a three-dimensional image representative of the patient's brain;

performing registration to align the three-dimensional image with a reference image, using 3-D rigid and/or non-rigid transformations;

identifying regions in the aligned image that correspond to normal regions within a brain;

determining, from said aligned image, the attenuation of each of a plurality of first voxels or group of adjacent voxels within each identified region of the brain;

classifying each said first voxel or group of adjacent voxels within each identified region by a probability value that is derived from, and indicative of, a difference between the determined attenuation of a voxel or group of adjacent voxels and an expected attenuation of that voxel or group of adjacent voxels at that region of the brain, wherein said classifying in respect of each of said plurality of first voxels or group of adjacent voxels having a particular type of brain structure comprises determining, from the same said aligned image, the attenuation of a respective second voxel or group of voxels in a corresponding region on the opposite side of the brain having the same type of brain structure, comparing the determined attenuation of each said first voxel or group of adjacent voxels with the determined attenuation of a respective second voxel or grow of adjacent voxels to derive a value for the difference therebetween, and generating a respective voxel score comprising a said probability value indicative of said difference;

applying one or more probability values to each said identified region to generate a probability map of ischemic changes within the patient's brain, wherein each applied probability value is indicative of a strength of evidence of ischemia at a respective identified region; and deducing a cumulative score that combines the probability values from all the voxels of at least an identified region of the patient's brain.

2. A computer-implemented method as claimed in claim 1 wherein the probability value indicates a likelihood or probability of damage to a region of the brain represented by the voxel.

3. A computer-implemented method as claimed in claim 2 wherein the probability value is a value between 0 and 1.

4. A computer-implemented method as claimed in claim 1 wherein the probability value is also weighted to take account of the functional relevance of that part of the brain, by associating each voxel with a weight indicating an importance of a corresponding portion of brain tissue to patient outcome and disability, and the cumulative score combines the weighted probability value.

5. A computer-implemented method as claimed in claim 1 also comprising displaying two-dimensional tomographic images, and superimposing the voxel scores onto those two-dimensional images.

6. A computer-implemented method as claimed in claim 5 wherein the two-dimensional images are in black and white, and the voxel scores are superimposed on the images in a colour whose intensity represents the probability value.

7. A computer-implemented method as claimed in claim 6 wherein probability values representing an increase in attenuation are superimposed in a first colour while probability values representing a decrease in attenuation are superimposed in a second colour.

8. A computer-implemented method for obtaining an assessment of the severity and location of a stroke in a patient, the method comprising:

performing a three-dimensional computed-tomography scan of the patient's head;

processing data from the computed-tomography scan to produce a three-dimensional image representative of the patient's brain;

performing registration to align the three-dimensional image with a reference image, using 3-D rigid and/or non-rigid transformations;

identifying regions in the aligned image that correspond to normal regions within a brain;

determining, from said aligned image, the attenuation of each of a plurality of first voxels or group of adjacent voxels within each identified region of the brain;

classifying each said first voxel or group of adjacent voxels within each identified region by a probability value that is derived from, and indicative of, a difference between the determined attenuation of a voxel or group of adjacent voxels and an expected attenuation of that voxel or group of adjacent voxels at that region of the brain, wherein said classifying in respect of each of said plurality of first voxels or group of adjacent voxels having a particular type of brain structure comprises determining, from the same said aligned image, the attenuation of a respective second voxel or group of voxels in a corresponding region on the opposite side of the brain having the same type of brain structure, comparing the determined attenuation of each said first voxel or group of adjacent voxels with the determined attenuation of a respective second voxel or group of adjacent voxels to derive a value for the difference therebetween, and generating a respective voxel score comprising a said probability value indicative of said difference;

applying one or more probability values to each said identified region to generate a probability map of ischemic changes within the patient's brain, wherein each applied probability value is indicative of a strength of evidence of ischemia at a respective identified region; and deducing a cumulative score that combines the probability values from all the voxels of at least an identified region of the patient's brain.

9. A computer-implemented method as claimed in claim 8 wherein a probability value indicates a likelihood or probability of damage to a region of the patient's brain represented by the voxel.

10. A computer-implemented method as claimed in claim 8 wherein the probability value is weighted to take account of a functional relevance of that part of the brain, by associating each voxel with a weight indicating an importance of the corresponding portion of brain tissue to patient outcome and disability, and the cumulative score combines the weighted probability values.

11. A computer-implemented method as claimed in claim 8 wherein the step of processing the data comprises filtering.

12. A computer-implemented method as claimed in claim 11 wherein the step of processing the data comprises resampling.

13. A computer-implemented method for displaying information about the severity and location of a stroke in a patient, comprising:

performing a three-dimensional computed-tomography scan of the patient's head;

processing data from the computed-tomography scan to produce a three-dimensional image representative of the patient's brain;

performing registration to align the three-dimensional image with a reference image, using 3-D rigid and/or non-rigid transformations, to produce aligned images in multiple planes through the patient's skull;

identifying regions in the aligned image that correspond to normal regions within a brain;

determining, from said aligned image, the attenuation of each of a plurality of first voxels or group of adjacent voxels within each identified region of the brain;

classifying each said first voxel or group of adjacent voxels within an identified region by a probability value that is derived from, and indicative of, a difference between the determined attenuation of a voxel or group of adjacent voxels and an expected attenuation of that voxel or group of adjacent voxels at that region of the brain, wherein said classifying in respect of each of said plurality of first voxels or group of adjacent voxels having a particular type of brain structure comprises determining, from the same said aligned image, the attenuation of a respective second voxel or group of voxels in a corresponding region on the opposite side of the brain having the same type of brain structure, comparing the determined attenuation of each said first voxel or group of adjacent voxels with the determined attenuation of a respective second voxel or group of adjacent voxels to derive a value for the difference therebetween, and generating a respective voxel score comprising a said probability value indicative of said difference;

applying one or more probability values to each said identified region to generate a probability map of ischemic changes within the patient's brain, wherein each applied probability value is indicative of a strength of evidence of ischemia at a respective identified region; and displaying two-dimensional images calculated from the three-dimensional image data, on which the probability values are superimposed.

14. A computer-implemented method as claimed in claim 13 wherein the probability value indicates the likelihood or probability of damage to the region of the brain represented by the voxel.

15. A computer-implemented method as claimed in claim 13 wherein the step of processing the data comprises filtering.

16. A computer-implemented method as claimed in claim 15 wherein the step of processing the data comprises resampling.

17. A computer-implemented method according to claim 13, further comprising calculating a cumulative score that combines the probability values from all the voxels of at least an identified region of the patient's brain.

18. A computer-implemented method as claimed in claim 17 wherein the probability value is weighted to take account of a functional relevance of that part of the brain, by associating each voxel with a weight indicating the importance of a corresponding portion of brain tissue to patient outcome and disability, and the cumulative score combines the weighted probability values.

* * * * *